(12) United States Patent
Seger et al.

(10) Patent No.: US 8,913,132 B2
(45) Date of Patent: Dec. 16, 2014

(54) CAMERA SYSTEM AND METHOD FOR DETECTING THE SURROUNDINGS OF A VEHICLE

(75) Inventors: Ulrich Seger, Leonberg-Warmbronn (DE); Gerald Franz, Backnang (DE)

(73) Assignee: Robert Bosch GmbH, Stuttgart (DE)

( * ) Notice: Subject to any disclaimer, the term of this patent is extended or adjusted under 35 U.S.C. 154(b) by 465 days.

(21) Appl. No.: 13/129,787

(22) PCT Filed: Nov. 3, 2009

(86) PCT No.: PCT/EP2009/064488
§ 371 (c)(1),
(2), (4) Date: Jul. 25, 2011

(87) PCT Pub. No.: WO2010/076064
PCT Pub. Date: Jul. 8, 2010

(65) Prior Publication Data
US 2011/0273564 A1    Nov. 10, 2011

(30) Foreign Application Priority Data
Jan. 2, 2009    (DE) .......................... 10 2009 000 005

(51) Int. Cl.
| | |
|---|---|
| H04N 7/18 | (2006.01) |
| B60Q 1/00 | (2006.01) |
| G06K 9/00 | (2006.01) |
| G01N 21/85 | (2006.01) |
| G01N 21/55 | (2014.01) |
| B60S 1/08 | (2006.01) |
| B60R 11/04 | (2006.01) |
| H01Q 1/12 | (2006.01) |
| B60R 11/00 | (2006.01) |
| G01N 21/43 | (2006.01) |

(52) U.S. Cl.
CPC ............. *G01N 21/552* (2013.01); *B60S 1/0818* (2013.01); *B60S 1/0822* (2013.01); *B60S 1/0837* (2013.01); *B60S 1/0833* (2013.01); *H01Q 1/1271* (2013.01); *G06K 9/00791* (2013.01); *B60R 11/04* (2013.01); *B60R 2011/0026* (2013.01); *B60S 1/0844* (2013.01); *G01N 2021/435* (2013.01)
USPC ........... 348/148; 340/438; 382/104; 250/573; 250/574

(58) Field of Classification Search
CPC ............ B60R 11/04; B60R 2011/0026; B60R 2011/435; G01N 21/552; B60S 1/0818; B60S 1/0844; B60S 1/0822; B60S 1/0833; B60S 1/0837; G06K 9/00791; H01Q 1/1271
See application file for complete search history.

(56) References Cited

U.S. PATENT DOCUMENTS

| | | | |
|---|---|---|---|
| 6,681,163 B2 * | 1/2004 | Stam et al. .................. | 701/36 |
| 7,365,303 B2 * | 4/2008 | Pallaro ......................... | 250/221 |

(Continued)

FOREIGN PATENT DOCUMENTS

| | | |
|---|---|---|
| CN | 1181498 | 5/1998 |
| CN | 1370980 | 9/2002 |

(Continued)

OTHER PUBLICATIONS

International Search Report for PCT/EP2009/064488, dated Oct. 2, 2010.

*Primary Examiner* — Joseph Ustaris
*Assistant Examiner* — Jill Sechser
(74) *Attorney, Agent, or Firm* — Kenyon & Kenyon LLP

(57) ABSTRACT

A camera system for detecting the surroundings of a vehicle through a vehicle window pane (1), having a camera (2) having an image sensor (4), a first optical radiation (6) generated by the vehicle surroundings detectable by a sensor surface (10) of the image sensor (4), and a radiation source (3) for emitting a second optical radiation (7). At least a portion of the emitted second optical radiation (7) is detectable by the sensor surface (10) of the image sensor (4), and the portion of the second optical radiation (7) detected by the sensor surface (10) is a function of a state of window pane (1). The first and second optical radiation (6, 7) are jointly detectable via at least one partial area (8, 9) of the sensor surface (10). A method is also provided for detecting the surroundings of a vehicle employing the camera system.

20 Claims, 4 Drawing Sheets

(56) References Cited

U.S. PATENT DOCUMENTS

| | | |
|---|---|---|
| 2005/0206511 A1* | 9/2005 | Heenan et al. ............ 340/438 |
| 2006/0015905 A1 | 1/2006 | Lee |
| 2008/0121034 A1* | 5/2008 | Lynam et al. .......... 73/335.05 |

FOREIGN PATENT DOCUMENTS

| | | |
|---|---|---|
| CN | 101198031 | 6/2008 |
| DE | 1 974 933 | 12/1967 |
| DE | 10 2004 015 040 | 10/2005 |
| DE | 10 2006 008 | 8/2007 |
| DE | 10 2006 010 | 9/2007 |
| EP | 1 506 108 | 2/2005 |
| EP | 1 580 092 | 9/2005 |
| EP | 1 777 943 | 4/2007 |
| JP | 2003-315256 | 11/2003 |
| JP | 2007-318581 | 12/2007 |
| JP | 2008-182360 | 8/2008 |
| WO | WO 03/097420 | 11/2003 |
| WO | WO 2006/015905 | 2/2006 |

* cited by examiner (A-A')

(B-B')

CAMERA SYSTEM AND METHOD FOR DETECTING THE SURROUNDINGS OF A VEHICLE

BACKGROUND OF THE INVENTION

Cameras in vehicles for detecting the surroundings of a vehicle may be used in particular in driver assistance systems for functions such as night vision assistance, lane departure warning, traffic sign recognition, lighting assistance, and/or vehicle backup assistance.

The use of cameras for rain sensor systems in vehicles is also known. Published German patent application document DE 197 49 33 A1 discloses a method and a camera for detecting objects, such as water droplets or other soiling, present on a windshield of a motor vehicle. The camera is situated behind the windshield and is focused on the exterior of the windshield.

Camera systems are also known which are suitable for recording the surroundings of a vehicle as well as detecting a state of a vehicle window pane. Such a camera system is described in published German patent application document DE 10 2004 015 040 A1. This camera system includes a camera and a radiation source, the camera having an image sensor for recording images with the aid of which a first optical radiation generated by the vehicle surroundings is detectable, and the radiation source generating a second optical radiation which is detected by the image sensor. The second optical radiation which is detected by the image sensor is a function of the state of the window pane, in particular wetting of the window pane by raindrops. To achieve such a dependency, the second optical radiation which is emitted by the radiation source is coupled into the interior of the vehicle window pane in such a way that in the unwetted state of the vehicle window pane the second optical radiation undergoes one or multiple total reflections before a portion of the second optical radiation is coupled into the camera. The total reflection, and therefore the intensity of the second optical radiation which is detectable by the image sensor, is reduced as a result of wetting of the surface of the vehicle window pane. The measurement of this reduction may be used to ascertain the wetting of the vehicle window pane.

According to published German patent application document DE 10 2004 015 040 A1, the beam bundle of the second optical radiation which strikes the image sensor is shaped in such a way that only a small partial area of a sensor surface of the image sensor is irradiatable by the second optical radiation. The image data encompassed by this partial area are used to determine the state of the window pane. The remaining area of the sensor surface of the image sensor is used for recording the vehicle surroundings. The partial area of the image sensor which is irradiatable by the second optical radiation is concealed by a shutter in such a way that first optical radiation originating from the vehicle surroundings is blocked and is not able to strike this partial area. Such a camera system requires accurate guiding of the second optical radiation so that the latter does not irradiate the partial area of the sensor surface which is provided for detecting the vehicle surroundings. Furthermore, as a result of providing a shutter, the portion of the sensor surface of the image sensor which is available for detecting the vehicle surroundings, i.e., first optical radiation, is reduced. A shutter also represents an additional element for the camera system.

SUMMARY OF THE INVENTION

According to the present invention, a camera system and a method for detecting the surroundings of a vehicle are provided which also allow a state of the vehicle window pane to be determined. The camera has an image sensor having a sensor surface which includes at least one first partial area which detects the first optical radiation as well as the second optical radiation.

The first partial area of the sensor surface allows the vehicle surroundings to be detected via the exposure by first optical radiation. Interference due to overlapping by second optical radiation may be avoided as a result of the time-offset exposure. The image data generated by exposing a second partial area with second optical radiation may thus be evaluated for determining the state of the window pane. The second partial area which is exposed by second optical radiation may also be at least partially exposed by first optical radiation. The time offset in the exposure of the first and second partial areas allows the second partial area to be irradiated with a sufficiently high intensity so that, despite overlapping by first optical radiation, for example, a reliable determination of the state of the window pane is possible.

A shutter or similar means which protect the second partial area from first optical radiation and allow only second optical radiation to pass through is/are not necessary according to the present invention. In addition, it is not necessary to guide the second optical radiation in such a way that it essentially strikes only the second partial area of the sensor surface.

At least a partial area of the sensor surface, in particular the entire sensor surface, may be used for detecting the first optical radiation as well as the second optical radiation; i.e., individual sensors which form the sensor surface may be exposed by overlapping first optical radiation and second optical radiation. Since shutters and accurate beam guiding of the second optical radiation are no longer necessary, a simple design of the camera system is possible.

The image sensor may be made up of multiple separate units which form the sensor surface. However, the image sensor is preferably a single image sensor unit.

Exposure of the first partial area by second optical radiation may be prevented by deactivating the radiation source at the time of exposure, or, by bypassing or blocking, for example, preventing second optical radiation from striking the first partial area. An LED or a laser is preferably considered as a radiation source for generating the second optical radiation. The camera is preferably distantly focused.

Thus, according to the present invention it may be provided on the one hand that at least one partial area of the sensor surface is periodically exposed by second optical radiation in each image recording cycle. Alternatively or additionally, it is also possible according to the present invention for at least one partial area of the sensor surface to be exposed by the second optical radiation periodically, i.e., every nth time, in each image recording cycle.

A partial area or the entire sensor surface of the image sensor may thus be exposed by the first optical radiation between two nth image recording cycles in the absence of the second optical radiation. The image data detected in these image recording cycles may be used for recording the vehicle surroundings. The nth image recording cycles allow the image data of the partial area exposed by second optical radiation, which in particular may also be the entire sensor surface, to be used for determining the state of the window pane. Influence of the image recording of the vehicle surroundings by second optical radiation may be avoided in this way.

It is thus possible in the nth image recording cycle for the partial area exposed by the second optical radiation or the entire sensor surface to be additionally exposed, at least partially, by first optical radiation. For example, by providing sufficient intensity of the second optical radiation it may be ensured that radiation overlapping the second optical radiation, in particular first optical radiation, does not significantly influence the state of the window pane.

In addition, shutters which protect a partial area of the image sensor from first optical radiation, as well as exact beam guiding of second optical radiation, are not necessary in this specific embodiment. In particular, partial areas of the sensor surface of the image sensor may be used for detecting first optical radiation for recording the vehicle surroundings, as well as for detecting second optical radiation for ascertaining the state of the window pane.

According to the present invention, in an image recording cycle of the image sensor, the first partial area and the second partial area of the sensor surface may be exposed in a time-offset manner with respect to one another, the first partial area being exposed by first optical radiation in the absence of second optical radiation, and the second partial area being exposed by first optical radiation and second optical radiation. These partial areas may be reset in size and position, and in particular may migrate, from one image recording cycle to another.

In both variants for determining a state of the window pane, overlapping of first optical radiation, which is ascertained for detecting the vehicle surroundings, by second optical radiation is prevented, which otherwise could possibly interfere with detection of the vehicle surroundings. This allows second optical radiation to be generated with an intensity which makes it possible to determine the state of the window pane despite overlap with first optical radiation.

BRIEF DESCRIPTION OF THE DRAWINGS

The present invention is explained in greater detail below with reference to exemplary embodiments which are illustrated by several figures.

DETAILED DESCRIPTION OF THE INVENTION

Figure 1:
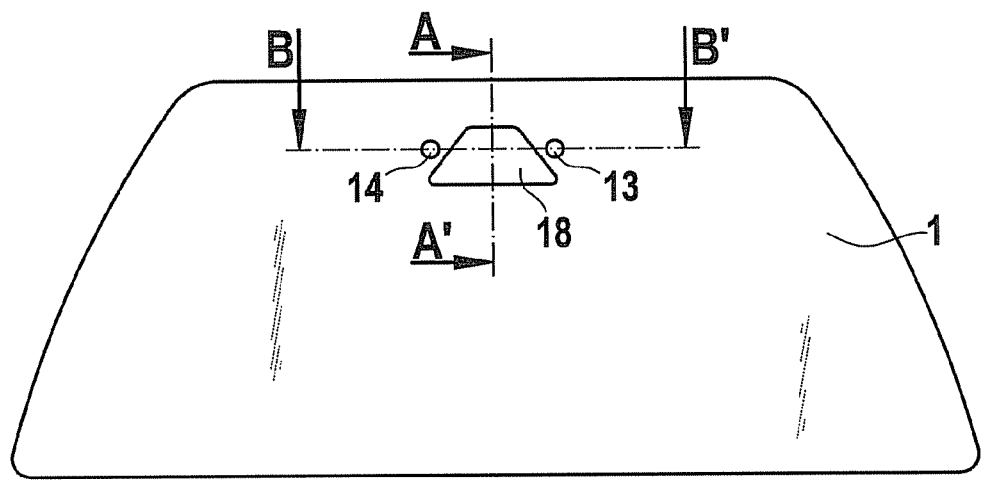
FIG. 1 schematically shows a window pane of a vehicle, indicating parts of one specific embodiment of a camera system according to the present invention.

Identical or corresponding components are denoted by the same or corresponding reference numerals in the figures.

Figure 2:
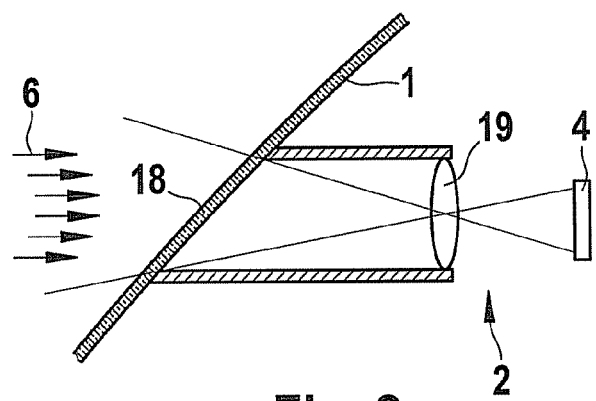
FIG. 2 shows a first sectional view of the camera system.
Figure 3:
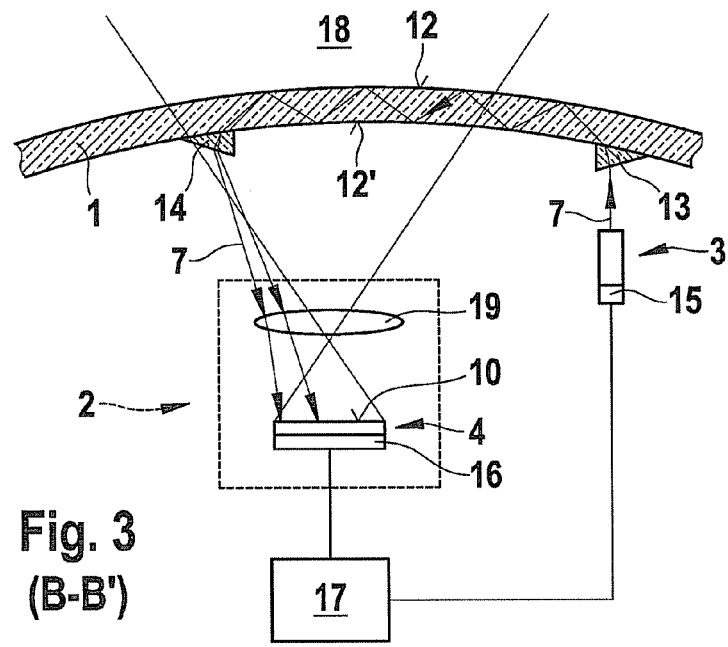
FIG. 3 shows a second sectional view of the camera system.

FIGS. 1 through 3 and FIG. 5 show one specific embodiment of a camera system according to the present invention for recording the surroundings of a vehicle and determining a state of a vehicle window pane 1, in the present case a windshield 1. FIG. 2 shows the section indicated by section line A-A' in FIG. 1, and FIG. 3 shows the section indicated by section line B-B'.

The camera system includes a camera 2 and a radiation source 3. Camera 2 has an image sensor 4 for recording images with the aid of which a first optical radiation 6 generated by the vehicle surroundings is detectable. Radiation source 3 may generate a second optical radiation 7, a portion of which is likewise detectable by image sensor 4. This portion of second optical radiation 7 detected by image sensor 4 is a function of the state of window pane 1, in particular of wetting of window pane 1 by raindrops. Image sensor 4 has a sensor surface 10, first optical radiation 6 as well as second optical radiation 7 being jointly detectable by at least a partial area of sensor surface 10. The camera system is designed in such a way that the state of window pane 1 is determinable using the portion of second optical radiation 7 which is detected by the partial area or the entire area of sensor surface 10.

In the present case camera 2 is a video camera. Image sensor 4 is a semiconductor-based image sensor, in the present case a CMOS image sensor. Alternatively, a CCD image sensor could be used. Sensor surface 10 of image sensor 4 has a plurality of pixels which form sensors 11 and which are provided in columns and rows in the form of a matrix. Radiation source 3 includes an LED. Alternatively, a laser may be used for radiation source 3. Radiation source 3 has a first control unit 15 for controlling the LED. Image sensor 4 includes a second control unit 16 for control. Camera 2 also includes camera optics 19, in the present case represented by a lens 19.

Camera 2 is situated in the interior of the vehicle, behind window pane 1 at the level of a vehicle rearview mirror, in such a way that first optical radiation 6 passing through window pane 1 is able to strike image sensor 4. In the present case this passage area 18 of the detection range of camera 2 is trapezoidal (see FIG. 1).

Before detection by image sensor 4, second optical radiation 7 may be guided in places through the interior of window pane 1. Second optical radiation 7 generated by radiation source 3 is coupled at an angle into the interior of window pane 1, via a first coupling means 13, in such a way that second optical radiation 7 is totally reflected on an exterior surface 12, and in the case of a window pane-air boundary interface, on a surface 12' of window pane 1 facing the vehicle interior. Second optical radiation 7 coupled-in this way passes horizontally through the visual cone of camera 2. A portion of the second optical radiation which has been reflected multiple times on surfaces 12, 12' is coupled out of window pane 1 and coupled into camera 2, via a second coupling means 14, in such a way that second optical radiation 7 is detectable by image sensor 4.

First coupling means 13 and second coupling means 14 are each formed by a prism situated at interior surface 12' of window pane 1. Alternatively, other optical elements, in particular diffractive elements, may be used for this function. The horizontal guiding of second optical radiation 7 through the interior of window pane 1 has the advantage that the components of the camera system needed for this purpose may be situated in particular behind a rearview mirror, which saves space and results in less interference from such a camera system.

A change in particular at outer surface 12 of vehicle window pane 1, for example as the result of wetting of surface 12 by water droplets, results in a reduction of the total reflections and a decrease in the intensity of the portion of second optical radiation 7 detected by image sensor 4. In addition, scattering of second optical radiation at one of surfaces 12, 12' of window pane 1, for example as the result of scratches, results in a decrease in intensity and/or a change in an intensity distribution of second optical radiation 7 at the location of image sensor 4.

The camera system also includes an evaluation unit 17. Evaluation unit 17 is connected to first control unit 15 of radiation source 3 and to second control unit 16 of image sensor 4 via data transmission lines. Evaluation unit 17 is responsible for evaluating image data detected by image sensor 4, in the present case for ascertaining the surroundings of a vehicle and determining a state of window pane 1. The connection to radiation source 3 and to image sensor 4 enables evaluation unit 17, to control radiation source 3, and image sensor 4 at appropriate points in time, and in particular allows activation and deactivation of the LED, as described in greater detail below. Evaluation unit 17 may be connected to further components, for example components of a vehicle assistance system.

According to one specific embodiment of a first method according to the present invention for recording the surroundings of a vehicle and detecting a state of vehicle window pane 1 (see FIGS. 4 and 5), in an image recording cycle 20 of image sensor 4 a first partial area 8 and a second partial area 9 of sensor surface 10 of image sensor 4 are exposed in a time-offset manner with respect to one another, first partial area 8 being exposed in the absence of second optical radiation 7, and second partial area 9 being exposed by second optical radiation 7. The exposure of first partial area 8 and second partial area 9 is time offset by the fact that xth pixel 11 is exposed after the exposure of the (x-y)th pixel is concluded.

In the present exemplary embodiment, a first address pointer passes line by line through all sensors, i.e., pixels 11, from the first line of sensor surface 10 to the last line of sensor surface 10. When the first address pointer reaches a pixel, the exposure of this pixel 11 is started. A second address pointer runs at a distance y behind the first address pointer. When a sensor 11 is addressed by the second address pointer, the exposure originally started by the preceding first address pointer is terminated. In particular, the exposure time of individual sensors 11 is determinable from the speed at which the address pointers pass through sensor surface 10, and from distance y. This principle is also referred to as the "rolling shutter" principle.

Figure 4:
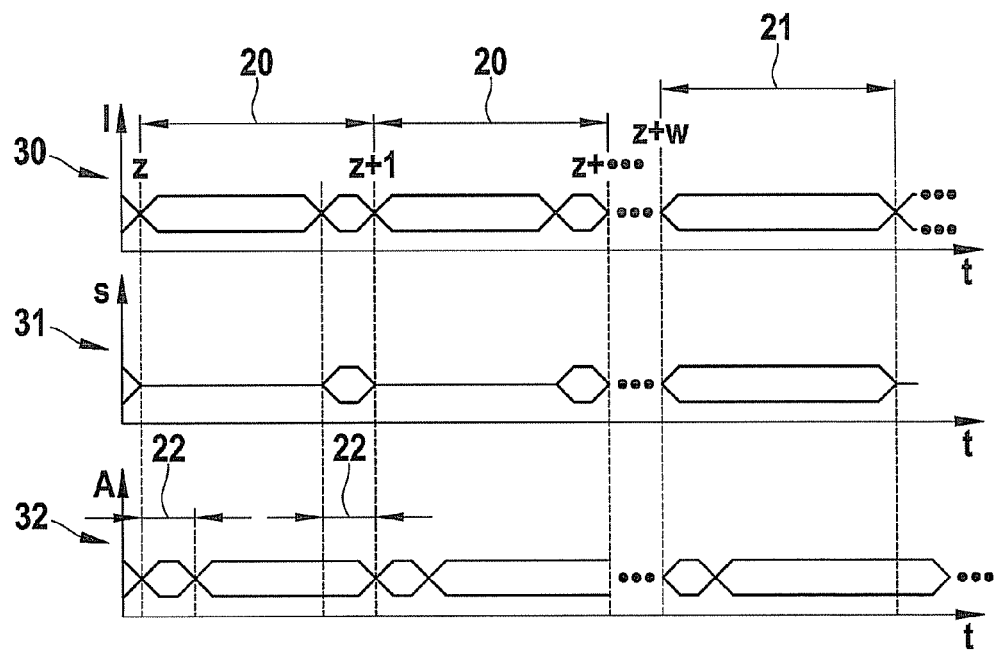
FIG. 4 shows three diagrams which represent the start of exposure and the end of exposure of an image sensor, and activation and deactivation of a radiation source of the camera system as a function of time.
Figure 5:
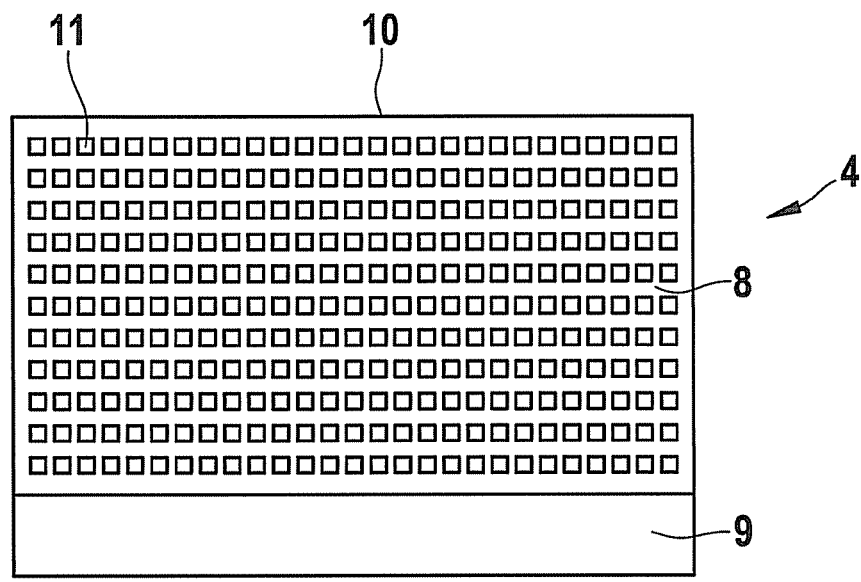
FIG. 5 shows a top view of a schematically illustrated sensor surface of the image sensor.

FIG. 4 shows three diagrams, first diagram 30 representing the start of exposure I of individual pixels 11 of sensor surface 10 as a function of time, second diagram 31 representing the state of the radiation source as a function of time, and third diagram 32 representing the conclusion of the exposure of individual pixels 11 of sensor surface 10 as a function of time.

To record a zth image, the exposure of sensor surface 10 is started in an image recording cycle 20. Sensor surface 10 is exposed according to the "rolling shutter" principle as described above. After the first address pointer, which starts the exposure of individual sensors 11, has passed through 95% of sensor surface 10, preferably 97.5% of sensor surface 10, with radiation source 3 deactivated, radiation source 3 is activated for passing through the remaining portion of sensor surface 10, so that second optical radiation 7 strikes sensor surface 10. When the first address pointer has passed through the entire sensor surface 10, which also indicates the end of an image cycle 20, radiation source 3 is switched off. The second address pointer runs behind the first address pointer at a distance which corresponds to exposure time 22 (see third diagram 32). In the present case, exposure time 22 in which each individual sensor 11 is exposed, corresponds to the period of time in which radiation source 3 is activated.

A sequence of w image recording cycles 20, in the present case w=25, is followed by a calibration cycle 21. Calibration cycle 21 differs from an image recording cycle 20 in that radiation source 3 is activated over the entire period of time which is required for the first address pointer to pass through the entire sensor surface 10.

First optical radiation 6, which is generated by the vehicle surroundings, strikes the entire sensor surface 10 for the entire period of time. In addition, second optical radiation 7 strikes sensor surface 10 during the time segments in which radiation source 3 is activated. As a result of the time offset of the exposure of individual sensors 11 of sensor surface 10, the entire sensor surface 10 is exposed by first optical radiation 6, but only a partial area 9 of sensor surface 10, which corresponds to a maximum of 10%, preferably a maximum of 5%, of the entire sensor surface 10 of image sensor 4, is exposed by second optical radiation 7. The region of sensor surface 10 which is exposed by first optical radiation 6 in the absence of second optical radiation 7 forms first partial area 8, and the other partial area of sensor surface 10 which is exposed by the first optical radiation and the second optical radiation forms second partial area 9.

Figure 6:
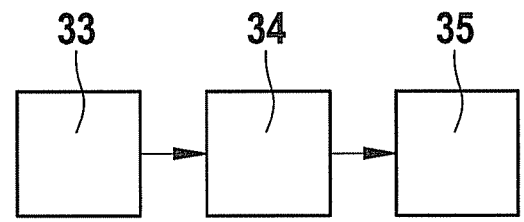
FIG. 6 shows a first flow chart for ascertaining a state of a window pane.

After each image recording cycle 20 or calibration cycle 21, the image data detected by sensor surface 10 are read out by evaluation unit 17 in a step 33 (see FIG. 6). For determining the state of the window pane, the image data of second partial area 9 are masked by a mask in a second step 34. The function of the mask is to reduce the influence of anomalies, such as scratches, which could impair the determination of the state of the window pane. In addition to complete masking of certain image data from second partial area 9, partial suppression of such data is possible. In a third step 35, the image data provided as a result of the masking are compared to reference values. The reference values may represent, for example, the state of an unwetted window pane 1. A difference between measured image data and reference values allows the state of the window pane to be determined. The reference values may be predefined values, or may have been formed by previously recorded image data. For example, for wetting of window pane 1 by raindrops the reference values may be formed by the image data which have been recorded by image sensor 4 in image recording cycles 20 shortly after a wiper operation. A comparison of these reference values to image data which are recorded shortly before a wiper operation allows the wetting of window pane 1 with raindrops to be determined. Formation of an average value of such reference values over a fairly long period of time allows the determination of long-lasting changes in the state of the window pane which may be caused, for example, by scratches, soiling, ice, or frost. Such reference values may also form the basis of a mask for masking image data, as described above.

The optical radiation is generated with sufficient intensity so that first optical radiation, which likewise is detected by second partial area 9, is not a factor in the evaluation of the state of the window pane.

Similarly, the image data obtained in calibration cycle 21, in which the entire sensor surface 10 is exposed by second optical radiation, may to determine the state of the window pane.

The position and/or the size of first partial area 8 and/or of second partial area 9 may be changed. For example, second partial area 9 may be allowed to "migrate" over sensor surface 10. First partial area 8 changes correspondingly. This migration may be achieved by activating radiation source 3 from image recording cycle 20 to image recording cycle 20, using different time offsets. In this way, in particular the entire sensor surface 10, when it is also time offset, may be used for detecting second optical radiation 7, although second partial area 9 is only a fraction of the total area of sensor surface 10.

By changing the period of time in which radiation source 3 is activated in an image recording cycle 20, the size of second partial area 9 of sensor surface 10 which is exposed by second optical radiation 7 may be changed from one image recording cycle 20 to another.

In one alternative specific embodiment of the method, a second partial area 9 is exposed by second optical radiation not in each image recording cycle 20, but, rather, periodically in each nth image recording cycle. N is preferably 10, and particularly preferably is in the range of 30 to 50.

According to one specific embodiment of a second method according to the present invention for recording the surroundings of a vehicle and determining a state of a vehicle window pane 1 (see FIGS. 7 and 8), sensor surface 10 of image sensor 4 is exposed in an image recording cycle of image sensor 4, at least one partial area of sensor surface 10, in this case the entire sensor surface 10, being periodically exposed by second optical radiation 7 in each nth image recording cycle 40'

Figure 7:
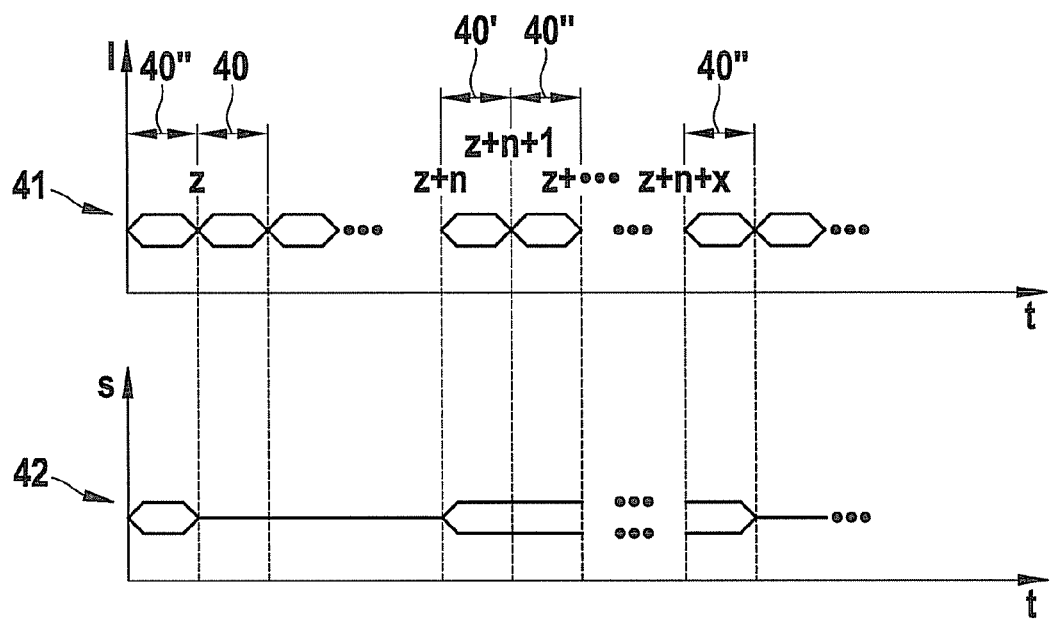
FIG. 7 shows two diagrams which represent exposure of the image sensor, and switching the radiation source of the camera system on and off as a function of time.
Figure 8:
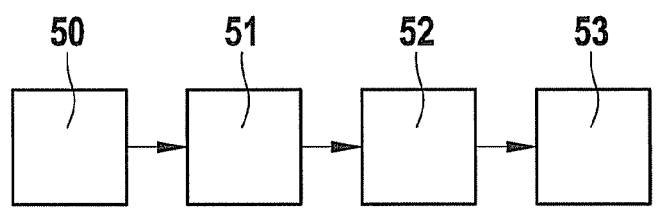
FIG. 8 shows a second flow chart for determining a state of a window pane.

FIG. 7 shows a first diagram 41 which represents exposure I of sensor surface 10 as a function of time, and a second diagram 42 which represents state s of radiation source 3, in the present case deactivated and activated, as a function of time. An image cycle is concluded when the entire sensor surface 10 has been exposed, as shown in first diagram 41. In each nth image recording cycle 40', in which in this case n 40, radiation source 3 is activated over the entire period of time that sensor surface 10 is exposed, so that sensor surface 10 is exposed by second optical radiation. This is followed by x additional image recording cycles 40", where x≥1, and x is preferably in the range of 2 to 7, in which radiation source 3 remains activated. Radiation source 3 is then activated, and this is followed by n−x−1 image recording cycles 40 in which second optical radiation 7 does not strike sensor surface 10. In addition to second optical radiation 7, first optical radiation 6, which is generated by the vehicle surroundings, continuously strikes the entire sensor surface 10, as the result of which sensor surface 10 is exposed in each of image recording cycles 40, 40', 40" by first optical radiation 6, optionally in addition to second optical radiation 7.

Evaluation unit 17 reads out the image data detected by sensor surface 10 in an image recording cycle 40, 40', and 40". The image data of image recording cycles 40', 40", in which sensor surface 10 has been exposed by second optical radiation 7, are used for determining the state of window pane 1. The image data of image recording cycles 40, which have been exposed in the absence of second optical radiation 7, represent the vehicle surroundings without interfering overlap by second optical radiation 7. These image data may also be further processed in evaluation unit 17, or may be relayed to other components within the scope of driver assistance functions.

For determining the state of the window pane, in a first step 50 (see FIG. 8) the image data of sensor surface 10, which have been recorded in image recording cycles 40', 40" with exposure by second optical radiation, are read out by evaluation unit 17. These image data are masked by a mask in a second step 51. The purpose of this masking is to mask image data which are unsuitable for the evaluation, which may be generated in window pane 1 due to scratches, soiling, or other anomalies, for example. Such masking may also optionally be dispensed with. In a third step 52, an average value is formed from the image data of nth image recording cycle 40' and x subsequent image recording cycles 40", in which radiation source 3 is continuously activated. The purpose of this average value formation in particular is to suppress noise. The image data which are masked and averaged in this way are compared to reference values in a fourth step 53. A deviation from the reference values indicates a change in the state of the window pane. The reference values may be formed using previously established values, or using image data previously recorded by image sensor 4. For example, for wetting of window pane 1 by raindrops the reference values may be formed by the image data which have been recorded by image sensor 4 in image recording cycles 40', 40" shortly after a wiper operation. A comparison of these reference values with image data which are recorded shortly before a wiper operation allows the wetting of window pane 1 by raindrops to be determined. An average value formation of such reference values over a fairly long period of time allows the determination of long-lasting changes in the state of the window pane which may be caused, for example, by scratches, soiling, ice, or frost. Such reference values may also form the basis of a mask for masking image data, as described above.

The image data which have been obtained in image recording cycles 40', 40" represent the exposure by second optical radiation as well as the exposure by first optical radiation 6. To suppress first radiation 6 for determining the state of the window pane, the intensity of second optical radiation 7 is set at a suitably high level. This is not a problem for detecting the vehicle surroundings, since the vehicle surroundings are detected in image recording cycles 40 in which radiation source 3 is not activated, i.e., image sensor 4 is not exposed by second optical radiation 7.

What is claimed is:

1. A camera system for detecting the surroundings of a vehicle through a vehicle window pane, comprising:
    a camera having an image sensor for recording images, wherein there is at least one image recording cycle, a first optical radiation generated by the vehicle surroundings being detectable by a sensor surface of the image sensor, and
    a radiation source for emitting a second optical radiation, wherein at least a portion of the emitted second optical radiation is detectable by the sensor surface of the image sensor, and the at least a portion of the emitted second optical radiation detected by the sensor surface of the image sensor is a function of a state of the vehicle window pane, wherein the second optical radiation is periodically coupled-in not in every image recording cycle but only in each nth image recording cycle, and
    the first optical radiation and the second optical radiation are jointly detectable via at least one partial area of the sensor surface of the image sensor.

2. The camera system as recited in claim 1, wherein the at least a portion of the emitted second optical radiation which is detected by the sensor surface of the image sensor is a function of wetting of the vehicle window pane by a liquid, scratches or indentations in the vehicle window pane.

3. The camera system as recited in claim 1, wherein the camera system is set up in such a way that the state of the vehicle window pane is determinable using the second optical radiation which is detected by the partial area.

4. The camera system as recited in claim 1, wherein the camera system further comprises a first controller that controls the radiation source, a second controller that controls the image sensor, and an evaluator that evaluates image data recorded by the image sensor.

5. The camera system as recited in claim 1, wherein in the image recording cycle a first partial area and a second partial area of the sensor surface of the image sensor are provided for exposure in a time-offset manner with respect to one another, the first partial area being exposed in the absence of the second optical radiation, and the second partial area being exposed by the second optical radiation.

6. The camera system as recited in claim 5, wherein the second partial area corresponds to a maximum of 10% of the entire sensor surface of the image sensor.

7. The camera system as recited in claim 6, wherein the second partial area corresponds to a maximum of 5% of the entire sensor surface of the image sensor.

8. The camera system as recited in claim 1, wherein, at least before detection by the image sensor, the second optical radiation is guided through the interior of the vehicle window pane in places and is reflected at least once on a surface of the vehicle window pane.

9. The camera system as recited in claim 1, wherein the camera system has a first coupling means and a second coupling means,
   wherein the at least a portion of the emitted second optical radiation which is a function of the state of the window pane may be coupled out of the vehicle window pane and coupled into the camera with the aid of the first coupling means, and the second optical radiation which is generated by the radiation source may be coupled into the window pane with the aid of the second coupling means.

10. The camera system according to claim 9, wherein the first and second coupling means are optical elements.

11. The camera system as recited in claim 1, wherein at every nth image recording cycle where the second optical radiation is coupled-in, the second optical radiation remains activated for more than one consecutive image recording cycle.

12. A method for detecting the surroundings of a vehicle, comprising:
    detecting a first optical radiation generated by the vehicle surroundings using an image sensor,
    generating a second optical radiation using a radiation source and guiding the second optical radiation through the vehicle window pane,
    detecting a portion of the second optical radiation which is a function of a state of the window pane by the image sensor,
    in at least one image recording cycle of the image sensor exposing at least one partial area of a sensor surface of the image sensor by the first optical radiation and the second optical radiation, wherein the second optical radiation is periodically coupled-in not in every image recording cycle but only in each nth image recording cycle, and
    determining the state of the window pane using the first radiation and second optical radiation detected by the partial areas.

13. The method as recited in claim 12, wherein the sensor surface of the image sensor has a first partial area and a second partial area which are exposed or read out in a time-offset manner with respect to one another,
    the first partial area being exposed in the absence of the second optical radiation, and
    the second partial area being exposed by the second optical radiation and at least partially exposed by the first optical radiation.

14. The method as recited in claim 13, wherein image data detected by the first partial area and the second partial area of the sensor surface of the image sensor are read out during or after an image recording cycle, the image data of the second partial area being evaluated for determining the state of the window pane.

15. The method as recited in claim 12, wherein the first partial area and the second partial area are exposed by the second optical radiation in a calibration cycle which is subsequent to an image recording cycle.

16. The method as recited in claim 12, wherein for determining the state of the window pane the image data of the first partial area and of the second partial area are compared to reference values, and on the basis of the comparison of the image data to the reference values a mask is created for image data of the second partial area, and image data of the second partial area are masked by the mask before the state of the window pane is determined.

17. The method as recited in claim 12, wherein the position or the size of the first partial area or of the second partial area are changed for a further subsequent image recording cycle.

18. The method as recited in claim 12, wherein n is greater than 10.

19. The method as recited in claim 18, wherein n is 30 to 50.

20. The method as recited in claim 12, wherein at every nth image recording cycle where the second optical radiation is coupled-in, the second optical radiation remains activated for more than one consecutive image recording cycle.

* * * * *